United States Patent
Quigley et al.

(10) Patent No.: US 10,512,561 B2
(45) Date of Patent: Dec. 24, 2019

(54) ARM SUPPORT

(71) Applicant: BeMe Innovations LLC, Lino Lakes, MN (US)

(72) Inventors: Benita Ann Quigley, Roseville, MN (US); Rebecca Leigh Welk, Lino Lakes, MN (US)

(73) Assignee: Lo-Hi Medical Designs, LLC, Excelsior, MN (US)

( * ) Notice: Subject to any disclaimer, the term of this patent is extended or adjusted under 35 U.S.C. 154(b) by 834 days.

(21) Appl. No.: 14/800,164

(22) Filed: Jul. 15, 2015

(65) Prior Publication Data

US 2017/0014259 A1 Jan. 19, 2017

(51) Int. Cl.
*A61F 5/37* (2006.01)

(52) U.S. Cl.
CPC .................. *A61F 5/3738* (2013.01)

(58) Field of Classification Search
CPC ....... A61F 5/3738; A61F 5/3723; A61F 5/373
USPC ............................................................ 602/4
See application file for complete search history.

(56) References Cited

U.S. PATENT DOCUMENTS

| | | | |
|---|---|---|---|
| 3,371,663 A | 3/1968 | Apgar | |
| 3,554,194 A | 1/1971 | Johnson | |
| 4,598,702 A | 7/1986 | Lilla | |
| 4,622,961 A * | 11/1986 | Christensen | .......... A61F 5/3738 602/4 |
| 4,759,353 A | 7/1988 | Melendez et al. | |
| 4,895,142 A | 1/1990 | Liptak | |
| 6,485,445 B1 * | 11/2002 | Hiltner | .................... A61F 5/373 128/845 |
| 6,659,971 B2 | 12/2003 | Gaylord | |
| 6,923,778 B1 | 8/2005 | Cheng | |
| 6,976,971 B2 | 12/2005 | Scudere | |
| 6,979,303 B2 * | 12/2005 | Jestrabek-Hart | ...... A61F 5/3738 2/45 |

(Continued)

FOREIGN PATENT DOCUMENTS

WO WO-2017011781 A1 1/2017

OTHER PUBLICATIONS

"International Application Serial No. PCT/US2016/042586, International Preliminary Report on Patentability dated Jan. 25, 2018", 10 pgs.

(Continued)

*Primary Examiner* — Kari K Rodriquez
*Assistant Examiner* — Camtu T Nguyen
(74) *Attorney, Agent, or Firm* — Schwegman Lundberg & Woessner, P.A.

(57) ABSTRACT

An arm support for transferring and supporting a force corresponding to at least a portion of the weight of a supported arm. The arm support including a force distribution portion and a support portion. The force distribution portion adapted to conform to the shoulder of the unsupported arm and to distribute the force to the shoulder girdle, while the support portion supports the affected arm. The force distribution portion extends from a first end portion to a second end portion. The support portion extends from a first end portion to a second end portion. The support portion first end portion is located adjacent the force distribution portion second end portion and the support portion second end portion is configured to be adjustably couplable to the force distribution portion first end portion.

19 Claims, 11 Drawing Sheets

(56) References Cited

U.S. PATENT DOCUMENTS 7,179,241 B2 *   2/2007   Hollister ............... A61F 5/3738
                                                      602/20
2012/0245498 A1   9/2012   Krenzel
2013/0296756 A1 * 11/2013   Troncoso ................ A61F 5/026
                                                      602/19

OTHER PUBLICATIONS

"International Application Serial No. PCT/US2016/042586, International Search Report dated Oct. 14, 2016", 3 pgs.
"International Application Serial No. PCT/US2016/042586, Written Opinion dated Oct. 14, 2016", 8 pgs.
International Patent Application No. PCT/US2016/042586, International Search Report and Written Opinion dated Nov. 4, 2016, 12 pages.

* cited by examiner

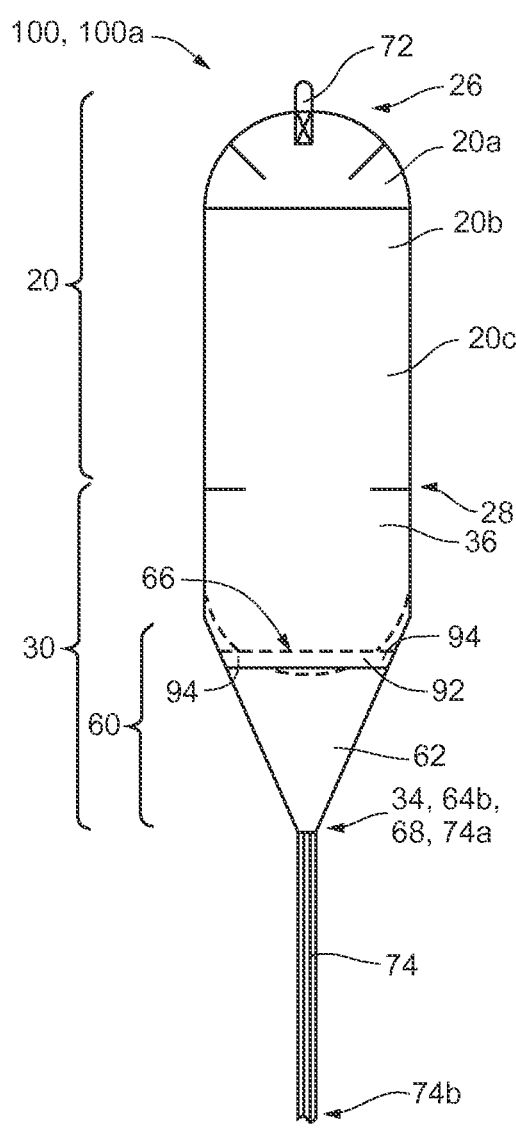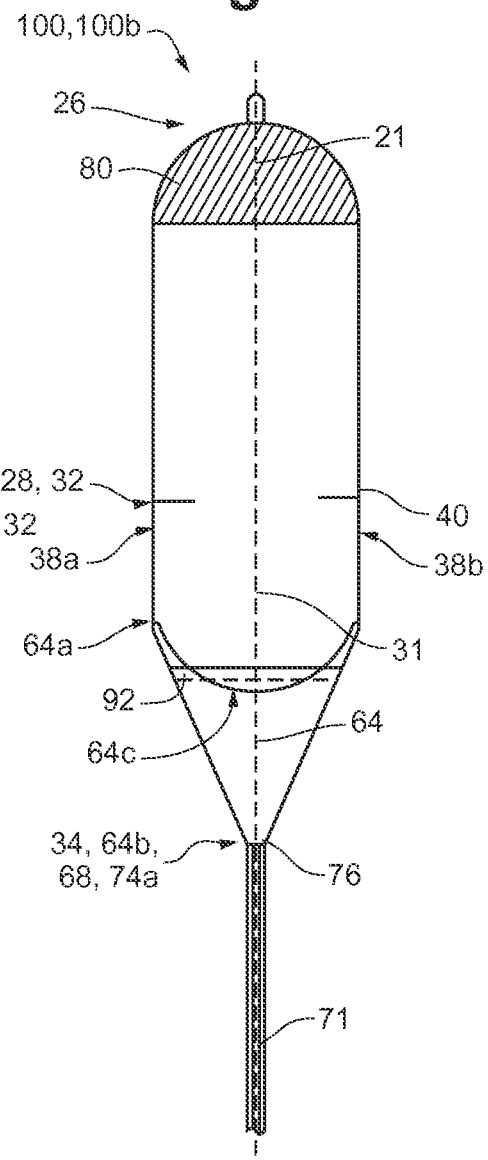

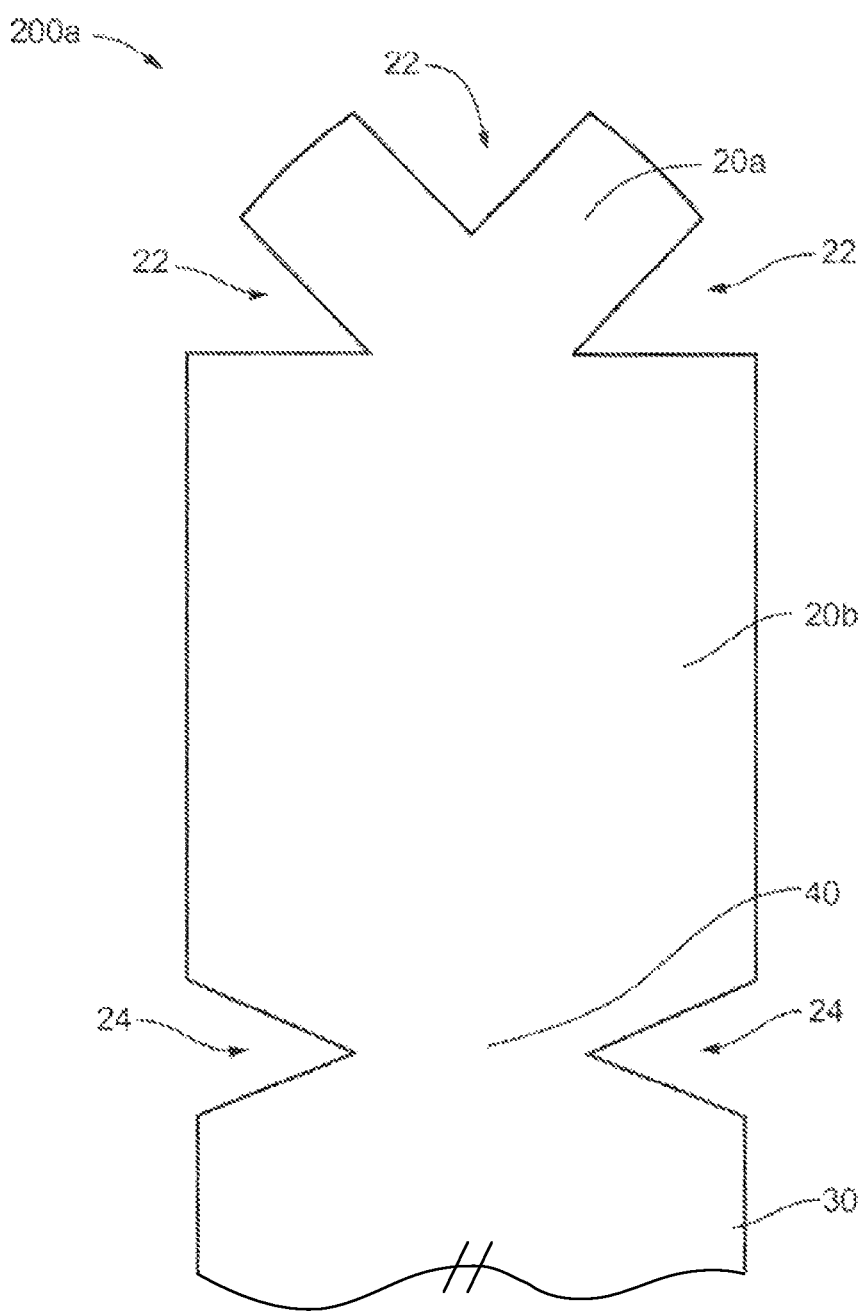

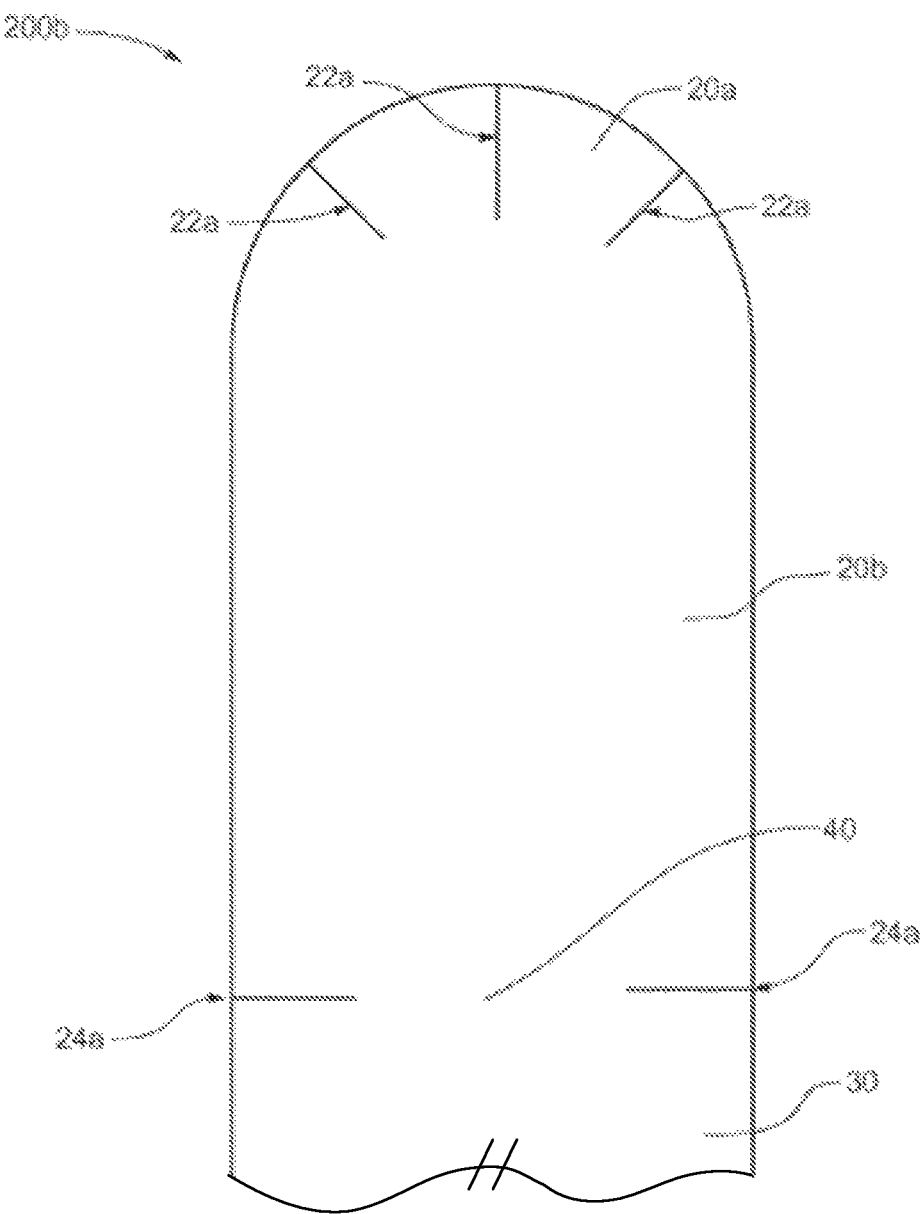

72

ARM SUPPORT

BACKGROUND

The medical and physical therapy fields have employed upper extremity supports including arm supports (e.g., slings) for years in order to stabilize an arm and provide rest to an arm and adjacent muscles and bones to treat an injury. In particular, slings are used to support and immobilize an arm. Although conventional slings may provide some immobilization and support, they often put undesirable strain on the shoulder and neck area of the user. In general, conventional slings have one narrow strap over the unaffected shoulder. This strap most often rests in the curve between the shoulder and neck. This placement and added downward force from the injured arm (often casted) irritates and impinges on tissues of that region of the neck. The discomfort of conventional strap designs often causes a level of discomfort that leads to lack of compliance. This lack of compliance is prevalent, even amongst patients that are required to wear an arm support for proper healing.

The arm support or upper extremity sling of the present invention eliminates shoulder and neck impingement syndromes caused by the currently used and widely prescribed conventional arm slings.

SUMMARY

In general, this disclosure is directed to arm support devices including upper extremity and arm slings.

Beneficial aspects of the arm support disclosed herein include:
  i) more comfortable fit
  ii) simple one-handed adjustment by user (e.g., patient)
  iii) supports hand but provides easy egress of hand from arm support
  iv) convertible between different positions that may lead to reduced edema.

Described is an illustrative embodiment of an arm support for transferring and supporting a force corresponding to at least a portion of the weight of a supported arm of a user onto an opposite unsupported shoulder of the user. The illustrative embodiment of the arm support includes a force distribution portion and a support portion. The force distribution portion is adapted to conform to the shoulder of the unsupported arm. The force distribution portion is configured to distribute the force to the shoulder girdle on the unsupported side of the user's body. In the illustrative embodiment, the force distribution portion extends from a first end portion to a second end portion opposite the first end portion. The support portion extends from a first end portion to a second end portion opposite the first end portion. The support portion first end portion is adjacent the force distribution portion second end portion and the support portion second end portion is configured to be adjustably couplable to the force distribution portion first end portion.

In a second embodiment of an arm support for supporting a force corresponding to at least a portion of the weight of a supported arm of a user onto an opposite shoulder of the user (the user having a longitudinal axis extending along the user's erect spine from the waist to the head of the user). The arm support is adapted to convert the user's supported arm from a first position to a second position. The arm support includes a force distribution portion, a support portion, and an adjustment device.

In the second embodiment, the force distribution portion adapted to distribute the force across the shoulder girdle, the force distribution portion having a first end portion and a second end portion, the second end portion opposite the first end portion. The support portion is adapted to support at least a portion of the weight of the arm of the user, the support portion having a first end portion and a second end portion, the second end portion opposite the first end portion, the second end portion of the force distribution portion proximate the first end portion of the support portion. The adjustment device is coupled to the force distribution portion near the first end portion and to the support portion near the second end portion. The adjustment device includes: a locking element and an elongate adjustment member having an adjustment member first end portion and an adjustment member second end portion opposite the first end portion. The adjustment member being slidably couplable to the locking element between the first and second end portions of the adjustment member.

The arm support is configured to support the supported arm of the user in at least the first position and the second position when the first end portion of the force distribution portion is proximate the shoulder of the user. In the first position the user's lower arm and hand are arranged along a first axis substantially perpendicular to the longitudinal axis of the body of the user and proximate the waist of the user. In the second position, the lower arm and hand of the user are oriented along a second axis extending from the lower rib on the supported side of the user's body to the shoulder joint on the unsupported side of the user's body with the hand of the user located distal and elevated above the waist of the user with the user's hand supported such that the hand is proximate the pectoral muscle on the unsupported side of the user's body.

In a user friendly manner, the arm support is configured such that the arm support is convertible from the first position to the second position solely by moving the second end of the adjustment member away from the locking element in a substantially upward or downward direction along the longitudinal axis of the user using only the user's free hand.

The details of one or more examples are set forth in the accompanying drawings and the description below. Other features, objects, and advantages will be apparent from the description and drawings, and from the claims.

BRIEF DESCRIPTION OF DRAWINGS

FIG. 3a is a top view of an outer first surface of the arm support of FIG. 1.

FIG. 3b is a top view of an inner second surface of the arm support of FIG. 1 and FIG. 3a.

FIG. 4a is a top view of an illustrative embodiment of a portion of a pattern of a first layer of the arm support of FIG. 1 including elbow and shoulder darts.

FIG. 4b is a top view of the illustrative embodiment of the portion of the pattern of the first layer of the arm support of FIGS. 1 and 4a including joined regions elbow and shoulder darts.

DETAILED DESCRIPTION

Figure 1:
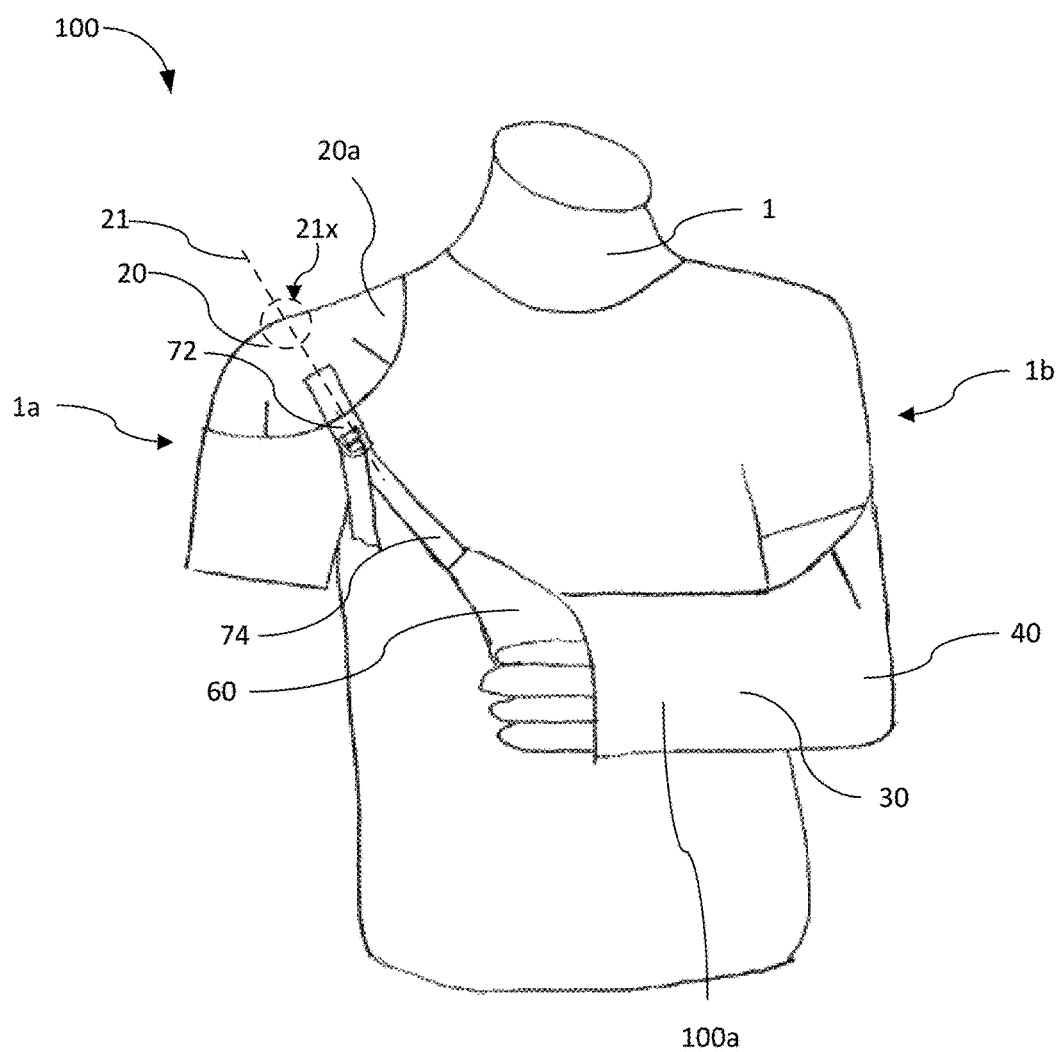
FIG. 1 is a front view of a user wearing an illustrative embodiment of an arm support oriented in a first position with the hand of the user egressed from a hand opening in the arm support.

The present disclosure will now be described more fully with reference to the Figures in which various embodiments of the invention are shown. The subject matter of this disclosure may, however, be embodied in many different forms and should not be construed as being limited to the embodiments set forth herein.

Embodiments of the present arm support improve the force distribution, and adjustment dynamics and components over conventional arm slings. The present invention provides increased comfort, decreased strain on the neck area, increased support of the shoulder, wrist and hand, and the ability to change arm, elbow and/or hand position for edema management.

The arm support 100 and its components may be used for any upper extremity injuries to provide support and comfort. The arm support, and in particular the shoulder girdle design and adjustment mechanism can also be used for products that are designed to support weight in the upper body or arms such as back packs, baby carriers, and breastfeeding accessories, etc.

Illustrative embodiments will be described with respect to an arm support 100 for supporting an affected arm (e.g., injured arm, supported arm 1b) on the supported side of the user's body 1b. In the illustrative embodiment of FIGS. 1-9, the opposite arm or side of the user's body to which the force of the supported arm 1b is transferred to, may be referred to as the unaffected or unsupported side of the user's body 1a (arm, shoulder, elbow, shoulder girdle, humerus, muscles, etc.).

Figure 2:
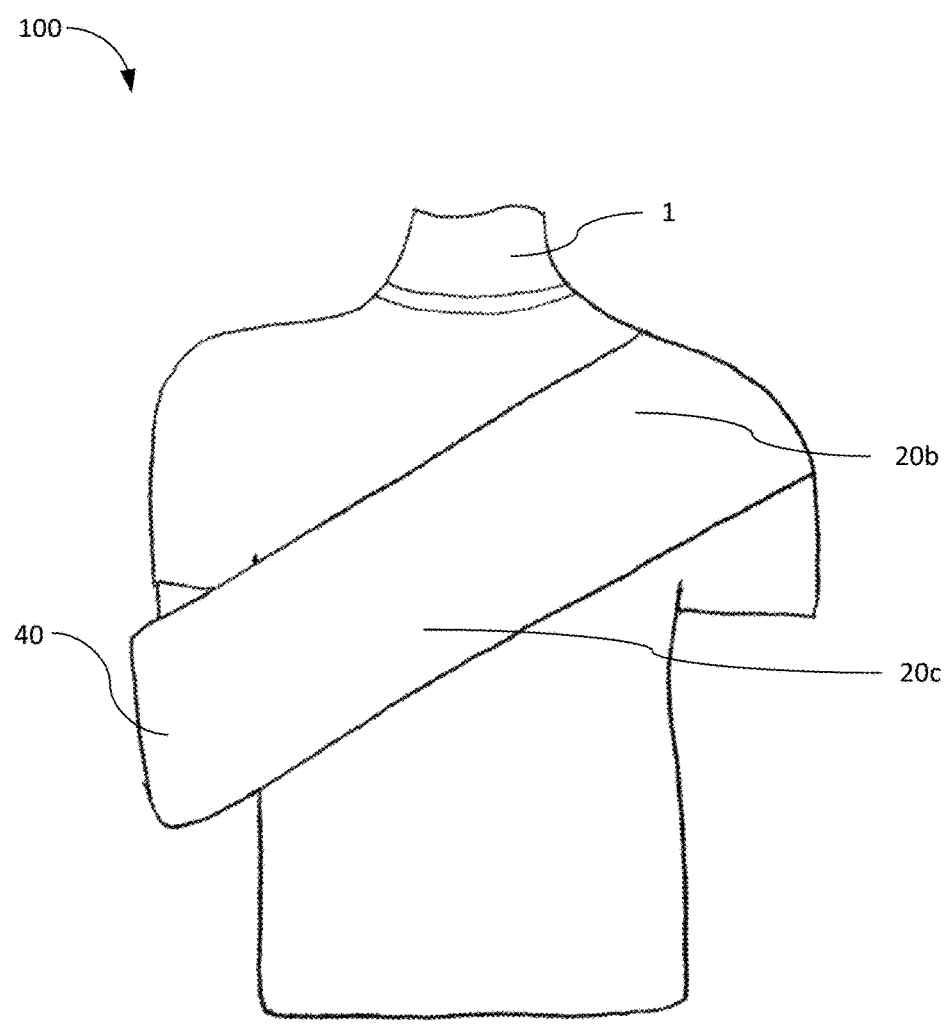
FIG. 2 is a rear view of the user wearing the arm support of FIG. 1.
Figure 5:
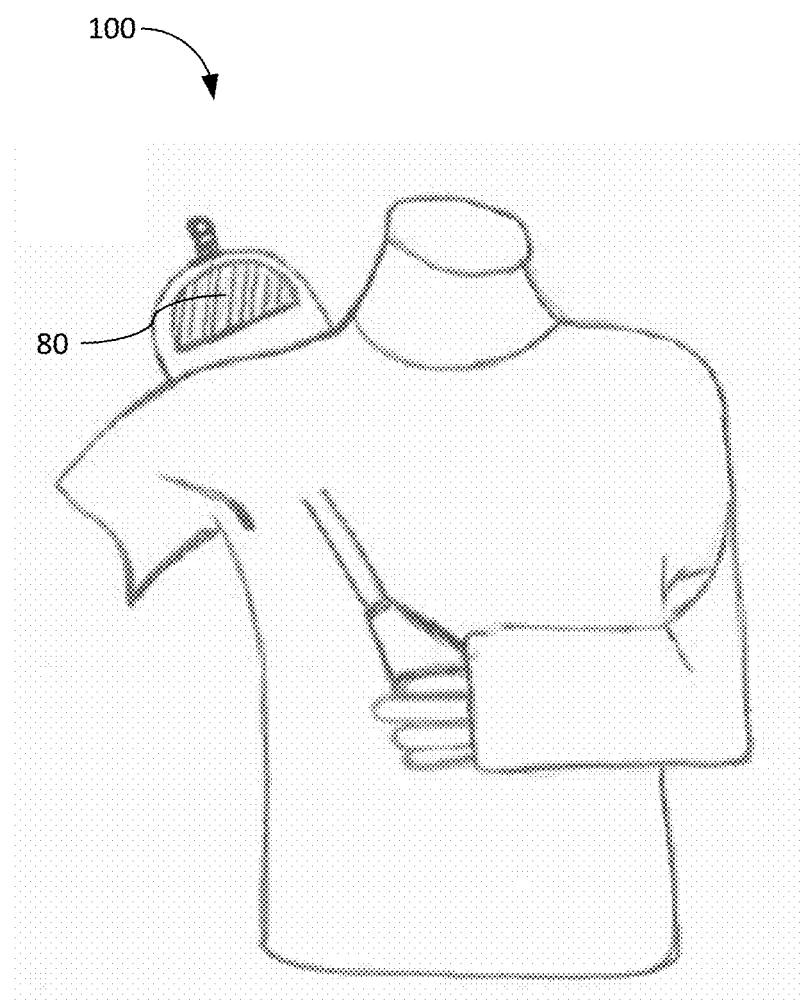
FIG. 5 is a front view of the user wearing the arm support of FIG. 1 with the adjustment device de-coupled and the fingers of the user egressed from the hand opening.
Figure 9A:
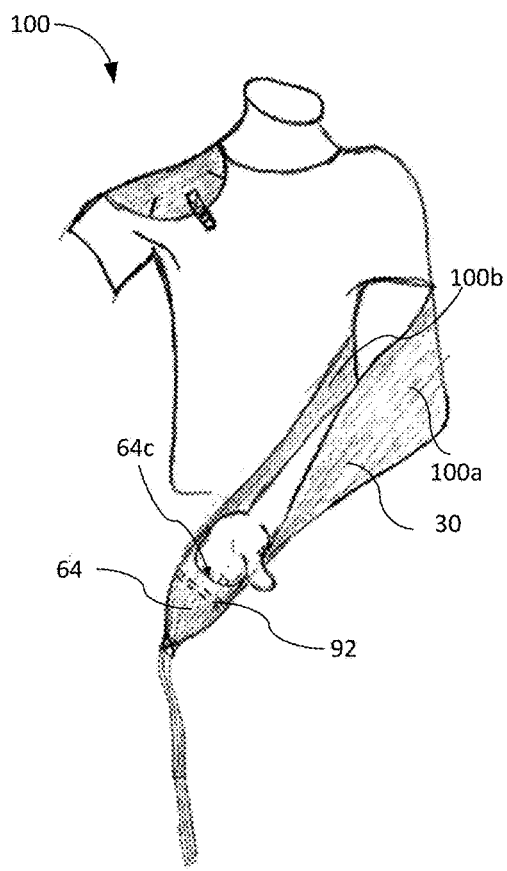
FIG. 9a is a front view of the user wearing the arm support of FIG. 1 with the adjustment device de-coupled and the fingers of the user tucked inside a hand support portion.

FIGS. 1 and 2 depict an illustrative embodiment of an arm support 100 for transferring and supporting a force corresponding to at least a portion of the weight of a supported arm 1b of a user 1 onto an opposite unsupported shoulder girdle of the user 1 (e.g., 1a). The arm support 100 has an outer first surface 100a, and an inner second surface 100b (FIGS. 3a, 3b and 9a). The arm support 100 may include a force distribution portion 20 adapted to be located over shoulder girdle (FIG. 11a, 11b) on the unsupported side of the user's body (e.g., 1a), a support portion 30 to support the affected/supported arm 1b, and an adjustment device 72, 74 to adjust the position of the supported arm 1b.

In the illustrative embodiment of FIGS. 1-9, the force distribution portion 20 includes a front shoulder cap 20a, a rear shoulder cap portion 20b and a back portion 20c to comfortably distribute the force of the supported arm 1b onto the unsupported shoulder girdle (FIG. 11a, 11b) and back (e.g., 1a) of the user 1. The support portion 30 includes an elbow portion 40 at one end of the support portion 30 to cradle the elbow, and a hand portion 60 at the other end of the support portion 30 to support the hand (e.g., 1b). The adjustment device 72, 74 includes a locking element 72 and an elongate adjustment member 74 (e.g., strap) to enable one handed-adjustment of the position of the supported arm (e.g., 1b). In some embodiments, the locking adjustment member 74 is slidingly engaged with the locking element 72 to facilitate adjustment of the arm support 100 to the user 1. In some embodiments the locking element 72 may be attached proximate (e.g., at, substantially in line with, near, adjacent, etc.) the mid-line 21 or mid-point 21x (FIGS. 1 and 3b) of the front shoulder cap 20a of the force distribution portion 20. When worn properly for maximum distribution of the force, the mid-point 21x is configured to be located at the clavicular-humeral joint of the user.

FIGS. 3a and 3b depict an illustrative embodiment of the general shape and construction of the arm support 100 when the adjustable member is decoupled from the locking element 72. As depicted, the shape of the arm support 100 differs substantially from conventional arm supports. The shape and construction work together to provide increased comfort and ease of adjustment for the user 1.

The shape of the arm support 100, when the adjustment member 74 is decoupled from the locking element 72, may be described as having the following elements arranged sequentially in the following order:

1) the front shoulder cap 20a has a generally semispherical or curved semi-circular shape (e.g., baseball cap or moon shape);

2) the rear shoulder cap portion 20b, back portion 20c, and a section of the support portion 30, form together a generally rectangular shape;

3) the hand portion 60 section of the support portion 30 is of a generally triangular or isosceles triangular shape (though the peak of the triangle may be cut off);

4) the adjustment member 74 is of a generally rectangular shape. The shapes are sized such that the diameter or width of the front shoulder cap 20a, the width of the rectangular portion, and the base of the isosceles triangle of the hand portion 60, all defined with respect to the direction perpendicular to the support axis 31, are of substantially similar dimensions. However, in contrast to the other components, the width of the adjustment member 74 is significantly less than the other width dimensions. In some embodiments the length of the adjustment member 74 along the adjustment member axis 71 is at least 10 times greater than the width of the adjustment member 74 (e.g., width is dimension perpendicular to the adjustment member axis 71). In some embodiments all of the aforementioned components are aligned or substantially aligned along the same support axis 31, as shown in FIGS. 3a and 3b. However, in some other embodiments the aforementioned components are aligned or substantially aligned along the same support axis 31, with exception of the adjustment member 74, which may be slightly angled with respect to the other components.

The layers of material that form the arm support 100 will now be described. The layers may be formed of any suitable fabric, either woven or non-woven, polymer sheets, or any other suitable material. In some embodiments, the arm support 100 is constructed of multiple overlapping layers (36, 62, 64). Each layer may be formed of one piece of material or more pieces of material. For example, FIG. 3a depicts a top view of the outer first surface 100a of the arm support 100 of FIG. 1. FIG. 3b is a top view of the inner second surface 100b of the arm support 100. As shown in the embodiment of FIGS. 3a and 3b, the force distribution portion 20 and support portion 30 of the arm support 100 are formed of a first layer 36. A separate hand portion first layer 62 overlaps with the first layer 36 at an overlap region 92 to form the main body of the arm support 100 (e.g., force distribution portion 20 and support portion 30).

Figure 7A:
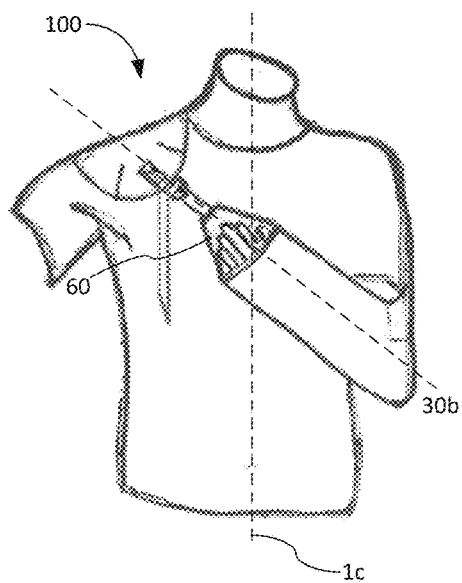
FIG. 7a is a front view of the user wearing the arm support of FIG. 1 oriented in the second position with the hand egressed from the arm support.
Figure 7B:
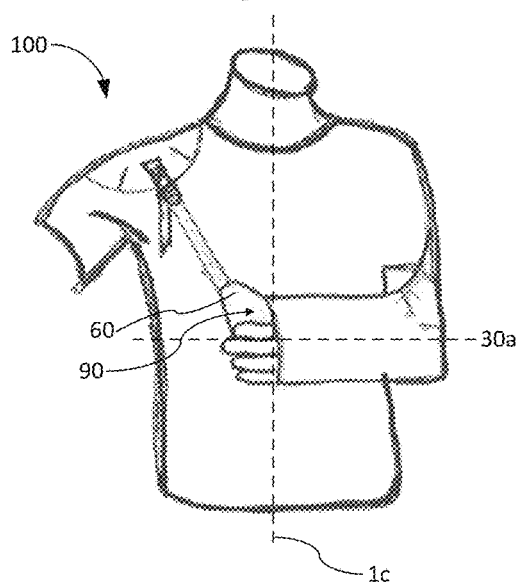
FIG. 7b is a front view of the user wearing the arm support of FIG. 1 oriented in the first position with the hand egressed from the arm support.
Figure 8:
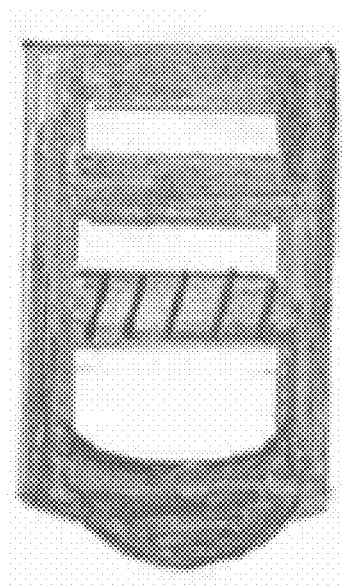
FIG. 8 is a top view of an illustrative embodiment of a locking element.

In addition to the first layer 36 and hand portion first layer 62, a second layer 64 may be provided in some embodiments for improved hand support and hand egress. Hand egress may be provided at hand access 90 (FIG. 7b). Second layer 64 will be described in further detail herein and with respect to FIGS. 9a, 9b and 10.

A main benefit of the arm support 30 is comfort for the user 1. The force distribution portion 20 plays a significant role in this increased comfort and improved support. In some embodiments, the force distribution portion 20 is adapted to conform to the shoulder of the unsupported arm (e.g., FIGS. 1-2, element 1a); and to distribute the force more evenly than conventional slings.

In some embodiments the force distribution portion 20 is described as having a shoulder girdle cap 20a, 20b that encompasses the entire unaffected shoulder girdle (FIGS. 11a-11b, in the area of elements 1d-1i) of the user 1. The components which form the shoulder girdle cap 20a, 20b include the front shoulder cap 20a and the rear shoulder cap portion 20b. This arrangement allows the force distribution portion 20 to conform to the anatomy of the shoulder girdle (FIGS. 11a-11b, in the area of elements 1d-1i) of the user 1. The force distribution portion 20 distributes the force to the shoulder girdle of the user 1, moving the pressure away from the neck and dispersing the weight through the unaffected shoulder and upper humerus (FIG. 11a, 10 and the upper back. This results in an increased comfort level during use and subsequently improves a patient's willingness to adhere to doctors and/or therapists orders to wear an arm support to immobilize the affected arm or shoulder (e.g., 1b).

In some embodiments, the front shoulder cap 20a includes a half moon shape that together with the rear shoulder cap portion 20b forms a baseball cap style design that sits over the unaffected/unsupported shoulder 1b when worn by the user 1. Another description of the shoulder cap 20a, 20b is that it may be a u-shaped component that helps distribute the weight evenly across the unsupported shoulder girdle of the user 1. The shoulder cap 20a, 20b is configured such that a mid-line 21 or a mid-point 21x of the shoulder cap 20a, 20b (see FIG. 1, front shoulder cap 20a) is positioned over the anterior head of the humerus (FIG. 11b, element 10 and pectoralis muscles (FIG. 11b, element 1h) to enable even distribution of force through and across the unsupported shoulder girdle (FIGS. 1-2, 1a and FIG. 11a).

For example, as shown in the arm support 100 pattern 200a of FIG. 4a (depicting a portion of the arm support 100 in the unjoined state), and the joined pattern 200b FIG. 4b (with seams joined), the front shoulder cap 20a may have a generally semi-circular portion with cutouts 22 on either side of sections of the front shoulder cap material 20a (FIG. 4a). The sections are joined together to form darts 22a (FIG. 4b). The resulting front shoulder cap 20a is of curved construction providing a 3-dimensional form such that the shoulder cap 20a, 20b conforms to the unsupported shoulder 1a of the user 1 to distribute the force evenly.

Figure 11A:
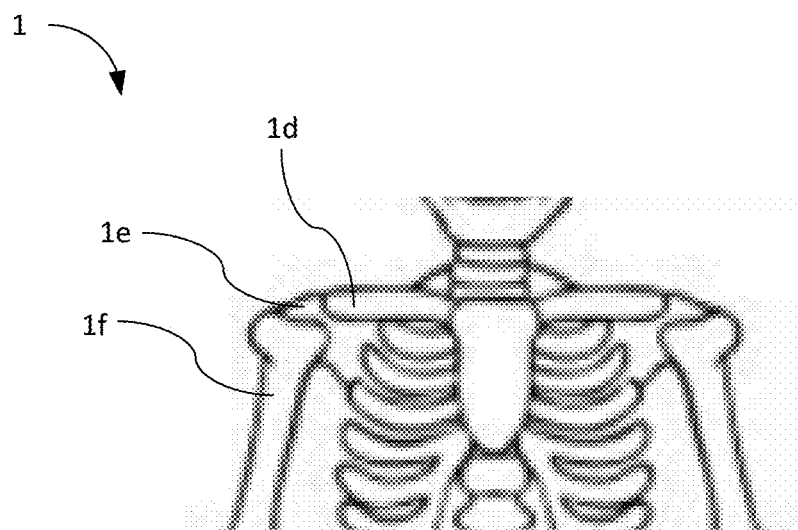
FIG. 11a is a front view of an upper torso portion of the skeletal structure of the user.
Figure 11B:
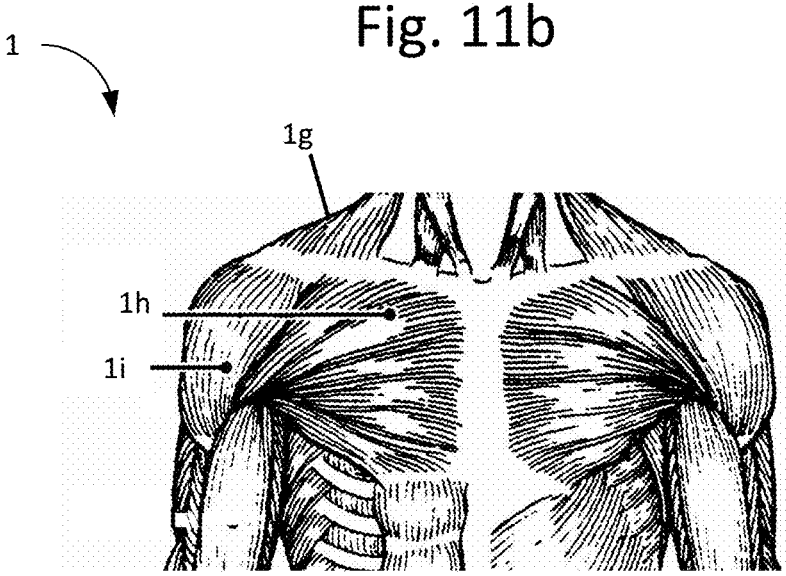
FIG. 11b is a front view of an upper torso portion of the muscular structure of the user.

With regard to the anatomy of the user 1 shown in FIGS. 11a-11b, the force distribution portion 20 construction is configured to fit distally over the deltoid muscle 1i and the shaft of the humerus 1f and medially over the clavicle 1d extending across the upper trapezius muscle 1g and scapula 1e. The force distribution portion 20 allows for even weight offloading throughout the shoulder girdle and back. This eliminates the direct force applied to the clavicle 1d, upper trapezius muscle 1g, and brachial plexus by traditional slings. This force distribution design mimics the internal anatomy of the shoulder girdle muscles (e.g., supraspinatus, infraspinatus, teres minor, and subscapularis) by allowing proper support, range of motion and eliminating direct force to any one area of the unsupported shoulder 1a.

FIGS. 3a and 3b show the entire arm support 100 laid out in a substantially planar form (to the extent that the arm support can be laid flat). The arrangement of various portions in the illustrative embodiment will now be described. The force distribution portion 20 extends from a first end portion 26 to a second end portion 28 opposite the force distribution portion first end portion 26.

Also, with reference to FIGS. 3a and 3b, the support portion 30 extends from a first end portion 32 to a second end portion 34 opposite the support portion first end portion 32. The support portion first end portion 32 is located adjacent the force distribution portion second end portion 28. In some embodiments the support portion second end portion 34 is configured to be adjustably couplable to the force distribution portion first end portion 26 via the adjustment device 72, 74.

In some embodiments at least a portion of the adjustment device 72, 74 is coupled to the front shoulder cap 20a. The adjustment device 72, 74 may include the locking element 72 attached to an outer first surface 100a of the arm support 100 and the adjustment member 74 attached to the support member 30 (or vice versa). The position of the locking element 72 coupled to the elongate adjustment member 74 provides a downward force that keeps the force distribution portion 20 in place and allows for an even distribution of weight when worn by the user 1.

A slip-reducing grip 80 (FIGS. 3b and 5) may be located opposite the locking element 72 on an inner second surface 100b of the arm support 100 to keep the shoulder cap 20a, 20b in the correct position. The correct position being over the anterior portion of the unsupported shoulder 1a. This prevents any posterior sliding of the sling and helps maintain optimal shoulder girdle positioning. The grip 80 may be made of rubber, silicone, or any other suitable friction enhancing and slip reducing material.

In addition to distributing weight evenly, the force distribution portion 20 also allows for full a full range of motion of the unaffected arm (e.g., unsupported arm 1a), with little or no movement of the force distribution portion 20 with respect to the user 1. The force distribution portion 20 is configured such that the user 1 may move and even elevate their unsupported arm 1a without creating a corresponding (e.g., equivalent) motion in the supported arm 1b. For example, the unsupported 1a elbow (e.g., 1a) can be raised out to the side up to the height of the shoulders with little or no movement of the supported arm 1b (e.g., 1b). In other words, for a motion of the unsupported 1a of a given magnitude, the motion in the supported arm 1b will be zero, or a negligible amount of motion that is only a fraction of the motion in the unsupported arm 1b. For example, for a given motion of the unsupported arm 1a, the supported arm 1b will move 30% or less of the given motion. In a preferred embodiment, the motion induced to the elbow of the affected arm will be 20% or less than the input motion introduced by the upper portion of the humerus 1f (FIG. 13, 10 of the unsupported arm 1a. In a particularly preferred embodiment, the motion induced to the elbow of the supported arm 1b will be 10% or less than the input motion introduced by the upper portion of the humerus 1f (FIG. 11, 10 of the unsupported arm 1a. In some embodiments, the upper portion of the humerus 1f (FIG. 13, 1f) may be defined as between 1 and 3 inches distal from the upper end of the humerus 1f (FIG. 13, 1f) at the shoulder joint (FIGS. 11a-11b).

The support portion 30 provides support to the supported arm 1b via contact with the lower portion of the user's arm and elbow (e.g., 1b). Referring to FIGS. 3a-3b, the support portion 30 has a length extending along a support axis 31. The length of the support portion 30 extends from the elbow portion 40 near the support portion first end portion 32 to the hand portion 60 near the support portion second end portion 34 (Also see FIG. 1). In some embodiments, the support portion 30 may be formed of the first layer 36 extending from the support portion first end portion 32 to an overlap region 92 closer to the support portion second end portion 34 than the support portion first end portion 32. The hand portion 60 including a separate hand portion first layer 62 extending from a hand portion first end portion 66 at overlap region 92 to a hand portion second end portion 68 (e.g., the support portion second end portion 34). The length of the hand portion from the first end portion to the second end portion of the hand portion may be dependent on the size of the user. In some embodiments the length may be between about 4-8 inches, or a minimum of about 4 inches. In a preferred embodiment, the hand portion length may be about 6-8 inches, or a maximum of about 8 inches. In a more preferred embodiment, the hand portion length may be about 5-7 inches, and most preferably about 6 inches.

In some embodiments, the support portion 30 may be described as having a width defined from a first longitudinal side end portion 38a to a second longitudinal side end portion 38b (FIG. 3b). In particular, the first longitudinal side end portion 38a may extend from the support portion first end portion 32 to the support portion second end portion 34. The second longitudinal side end portion 38b is located opposite the first longitudinal side end portion 38a and may extend from the support portion first end portion 32 to the support portion second end portion 34. The support portion 30 width extending from the first longitudinal side end to the second longitudinal side end. The support portion, the first layer 36 and the hand portion first layer 62 overlap one another in the overlap region 92 and are joined together at joining regions 94 (FIG. 3a) near the first and second longitudinal side end portions 38b, and wherein a portion therebetween remains unjoined to permit hand egress from the support portion 30 in the overlap region 92 when worn by the user 1.

Figure 9B:
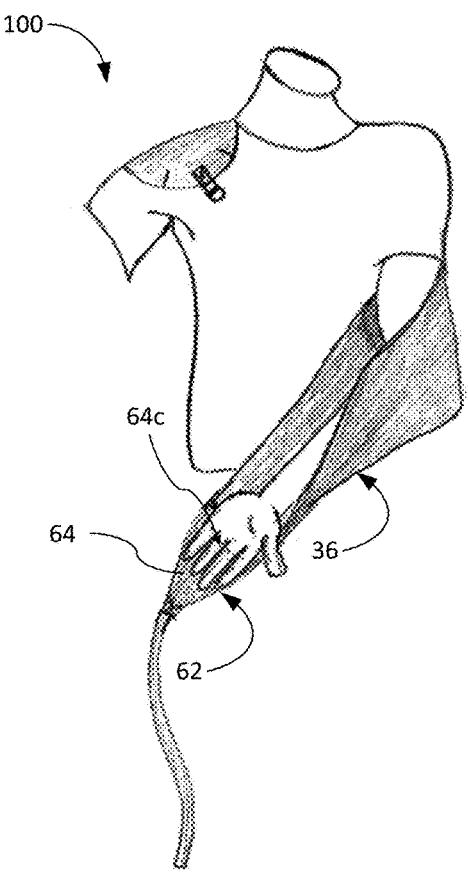
FIG. 9b is a front view of the user wearing the arm support of FIG. 1 with the adjustment device de-coupled and the fingers of the user not tucked inside a hand support portion.
Figure 10:
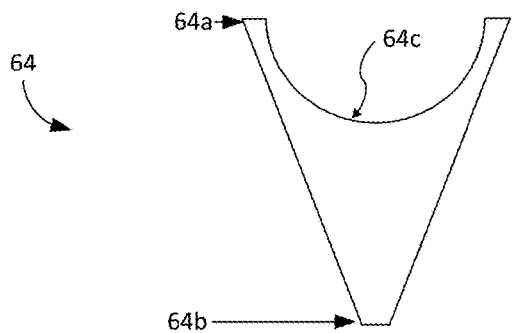
FIG. 10 is a top view of a second layer of the hand support portion of FIGS. 6a and 6b.

As perhaps best shown in FIGS. 3a, 3b, with additional insight provided in FIGS. 9a, 9b and 10, the hand portion 60 may also include a second layer 64 having an overall length extending from a second layer first end portion 64a to a second layer second end portion 64b opposite the second layer first end portion 64a. In some embodiments, at least portion of the second layer 64 crosses and extends beyond the overlap region 92 in both directions along the support axis 31. This allows the user various options for comfortable placement, support and use of the hand while wearing the arm support 100, yet still minimizing movement of the supported arm 1b. In some embodiments the overall length of the second layer is about 5-7 inches, and preferably about 6 inches. The minimum length from the curved region 64c to the second layer second end portion 64b is about 2-4 inches, and preferably about 3 inches.

In some embodiments the width of the support portion 30 at the hand portion 60 is substantially wedge-shaped and narrows in width towards the support portion second end portion 34.

In some embodiments, the second layer 64 may be a generally triangular-shaped pattern of same or a different material as the first layer 36 and/or hand portion 60 first layer 36. The second layer 64 may be joined (e.g. sewn, adhered, welded, etc.) to the inner first surface 100b at the support portion second end portion 34. The overlapping material of the first layer 36, the hand portion first layer 36, and the second layer 64 creates a slot positioned where the hand will be located within the sling.

In the illustrative embodiment, the half circle shaped curved region 64c (FIG. 3b, 10) creates space to remove the hand from the arm support 100 with ease and with minimal flexion at the wrist. The hand access 90 (e.g., slot) allows the patient to wear the hand cradled within the arm support 100 for comfort, or to ergonomically egress the hand from the arm support 100 for functional use. The curved region 64c is not limited to specifically a half circle shaped geometry. Any suitable shape which provides for ergonomic egress of the hand may be employed.

In some embodiments, as previously described, the support portion second end portion 34 is attached to the adjustment member 74. In some embodiments the adjustment member 74 may be an elongate adjustment member 74, such as a strap and the attachment may occur at a coupling point 76. The coupling point 76 may be the location where the support portion second end portion 34 connects to a first end portion 26 of the adjustment member 74.

In some embodiments the adjustment member 74 has a length extending from the first end portion 74a to a second end portion 74b along an adjustment member axis 71. In some embodiments the support axis 31 and the adjustment member axis 71 are arranged within +/−45 degrees of one another at the coupling point 76. In at least one preferred embodiment, the support axis 31 and the adjustment member axis 71 are arranged parallel to one another at the coupling point 76, but at least not more than +/−30 degrees of one another.

In some embodiments, and as shown in FIGS. 1, 3a, 3b, 4a and 4b, the elbow portion 40 is located near the transition between the force distribution portion 20 and the support portion 30. The elbow portion 40 may form a pocket for cradling the elbow of the user 1. To provide proper guidance and positioning of the arm, elbow darts 24a (FIG. 4b) formed by wedge-shaped cutouts 24 (FIG. 4a) joined together, may be located near the transition between the support portion 30 and the force distribution portion 20. The edges of the cutouts 24 may be joined via any suitable means to form darts 24a.

The hand portion 60 of the support portion 30 may include features to provide the user 1 both maximum comfort and maximum accessibility to and use of the supported hand 1a (e.g., 1a) of the user 1. The inside of the overlapping fabric is cut in a substantially curved, semi-circular, or moon shape to allow the hand to easily slide into and out of the arm support 100 for support, functional activities, and range of motion as needed; all while still providing proper support for the wrist.

Conventional arm supports (e.g., slings) often have a "one size fits all" sizing system. This causes a poor fit for the supported arm 1b. The hand of the supported arm 1b dangles out the end of the pocket of the sling. This is not only uncomfortable at the wrist but causes forward pressure at the forearm and hand causing the arm to slide forward and fall out of the sling entirely. This is yet another reason that leads to difficulty with proper use and increased discomfort and frustration for the user 1.

Figure 6:
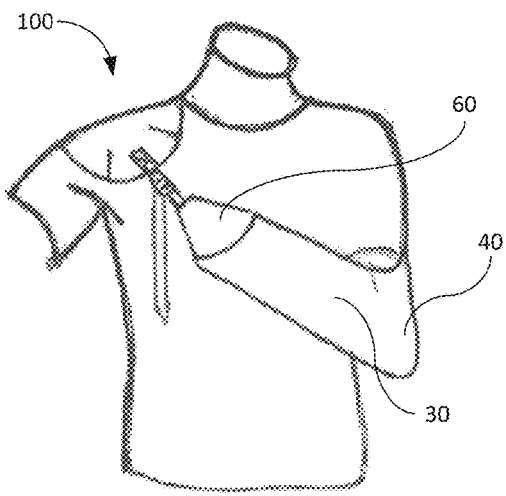
FIG. 6 is a front view of the user wearing the arm support of FIG. 1 oriented in a second position.

In one or more embodiments of the present invention, the arm support 100 provides the user 1 two options in relation to hand placement of the affected arm. As shown in FIGS. 6, 7a and 7b, the arm support 100 includes features that allow the user the option of supporting the hand within the arm support 30 (FIG. 6), or allowing the user to egress the hand from the arm support 30 (FIGS. 7a and 7b). Either option is available while supporting and restricting movement of the rest of the arm. With reference to FIGS. 3a and 3b, overlapping fabric at an overlap region 92 near the natural position of the hand creates a slot for the hand to egress from. This hand slot at the overlap region 92 allows the patient's hand to be supported but exposable for functional use and therapy. Secondly, the overlap creates a uniformed support to both the arm and the hand so both the arm and hand can be cradled within the sling for comfort and stabilization. In one or more embodiments, the overlap is at least 2 inches, or about 2-5 inches. In a preferred embodiment, the overlap is about 3 inches, or more preferably about 3.5 inches.

In some embodiments, hand access 90 is provided between the first longitudinal side end portion 38a and the second longitudinal side end portion 38b (FIG. 3b) of the support portion 30. In some preferred embodiments, the hand access 90 is provided centrally in between the first and second longitudinal side end portions 38a, 38b. In some embodiments, the overlapping portion of the hand access 90 extends all or a majority of the distance between the first and second longitudinal side end portions 38a to 38b.

As shown in the figures, the arm support 100 is provided to support a user 1's left arm. However, a mirror image arm support 100 for supporting the right arm is also within the scope of this disclosure. In some embodiments it is conceivable that the hand access would extend between the first or second longitudinal side end portion 38a or 38b and the support axis (only half way across the sling).

With regard to right hand vs. left hand arrangements, a single sling configuration may be capable of supporting either a right or left arm of the user (interchangeable). Any re-arrangement of parts to facilitate an arm support 100 to support a user's right arm as opposed to the user's left arm is deemed to fall within the scope of this disclosure.

To improve the ability to adjust the arm support 100 for both initial fit and for elevation of the supported hand 1b for comfort and edema control, an adjustment device 72, 74 is provided in some embodiments. In the illustrative embodiment of FIGS. 1-9, one such embodiment of the adjustment device 72, 74 is provided. The adjustment device 72 of the illustrative embodiment includes an elongate adjustment member 74 and a locking element 72 (see details of locking element in FIG. 8). The adjustment device 72 adjustably couples the force distribution portion 20 to the hand portion 60. In particular, the adjustment device 72 may be configured to adjust the distance between the force distribution first end portion 26 and the support portion second end portion 34 to facilitate adjustment of an angle of a lower portion of the supported arm 1b of the user 1 with respect to an upper portion of the supported arm 1b of the user 1.

The adjustment device 72 described herein is a user-friendly adjustment device 72. Benefits of the adjustment device 72 include:

i) enables a wide range of adjustment ii) provides one-handed adjustment using only the users unaffected arm iii) minimizes undesirable movement of the user's affected/supported arm during adjustment.

As shown in the illustrative embodiment of FIG. 3a, the elongate adjustment member 74 may be fixedly attached to the support portion 30 at coupling point 76. The adjustment member 74 extends from an adjustment member first end portion 74a to an adjustment member second end portion 74b. The adjustment member 74 may be configured to be slidably couplable to the locking element 72, and the locking element 72 may be coupled to the force distribution portion 20. The locking element 72 attachment to the force distribution portion 20 may be by a fixable attachment. The fixable attachment may be by a strap of material that is part of the locking element 72. The strap of material being located intermediate the force distribution portion 20 and the locking element 72, such as a 1 inch by 5 inch long strap as shown in FIG. 1. The strap and buckle being attached proximate (e.g., at, substantially in line with, near, adjacent, etc.) the mid-line 21 or mid-point 21x (FIGS. 1 and 3a) of the front shoulder cap 20a of the force distribution portion 20.

In some embodiments, for example, the adjustment device 72 may be a locking element 72 in the form of a 1 inch by 2 inch buckle or ladder lock; and an adjustment member 74 provided as a 1 inch strap. This is but one exemplary embodiment, any adjustment device 72 including an opposite or alternate arrangement of parts, or different parts is considered to be within the scope of this disclosure.

The adjustment device 72 allows each individual to uniquely adjust the arm support 100 to their needs and comfort by pulling the adjustment member 74 tighter or lifting the locking element 72 to loosen the adjustment member 74 easily with one hand. As shown in FIGS. 6, 7a-7b, as the adjustment member 74 is pulled tighter, it flexes the elbow past 90 degrees (e.g., past waist height such that an angle between the insides of the upper and lower arms is less than 90 degrees) to elevate the hand above the heart (e.g., above the waist). In a contrary motion, as the locking element 72 is lifted, the adjustment member 74 is loosened and it extends the elbow down. The adjustment device 72 may be manipulated as described to raise and lower the arm to the desired level.

In some embodiments, and as shown in FIGS. 6, 7a and 7b, the arm support 100 is configured to support the supported arm 1b of the user 1 in at least the first position (FIG. 7b) and the second position (FIGS. 6 and 7a), when the force distribution first end portion 26 is proximate the unsupported shoulder 1a of the user 1 as it would normally be worn.

In the first position the user's lower arm and hand is arranged along a first axis 30a substantially perpendicular to the longitudinal axis 1c of the body of the user 1 and proximate the waist of the user 1. In the second position, the lower arm and hand of the user 1 are oriented along a second axis 30b extending from the lower rib on the supported side of the user 1's body to the shoulder joint on the unsupported 1a side of the user's body with the hand of the user 1 located distal and elevated above the waist of the user 1, wherein the user's hand is supported such that the hand is proximate the pectoral muscle (FIG. 11a, 1h) on the unsupported 1a side of the user's body.

As depicted in FIGS. 6, 7a 7b, the arm support 100 is configured such that the arm support 100 is convertible from the first position (FIG. 7b) to the second position (FIGS. 6 and 7a) solely by moving the adjustment member second end portion 74b away from the locking element 72 in a substantially downward direction (e.g., toward the waist) along the longitudinal axis 1c of the user 1 using only the user 1's free hand. In an alternate embodiment where the locking element is attached to the support portion second end portion 34, and the adjustment member first end portion 74a is attached to the force distribution portion, the conversion may occur solely by moving the adjustment member second end portion 74b away from the locking element 72 in a substantially upward direction (e.g., toward the shoulders).

The adjustment member 74 length from the adjustment member first end portion 74a to the adjustment member second end portion 74b may be variable and be based on the size of the sling. When the adjustment member 74 is coupled to the locking element 72, the arm support 100 is joined into a continuous form for wrapping about the user.

The configuration of the force distribution portion 20 and the adjustment device 72 provides the unique benefit that the user 1 may elevate their unsupported arm 1a laterally 90 degrees at the shoulder joint without creating a corresponding motion in the supported arm 1b. In addition, the arrangement of the force distribution portion 20 and the adjustment device 72 act as a pivot point, preventing, reducing or minimizing transfer of motion of the unsupported arm 1a to the supported arm 1b.

One particular benefit of the invention is the ability to help control edema in the supported arm 1b. Many patients who suffer upper extremity injuries or surgeries complain of hand and finger pain and swelling. Swelling or edema control and management is often achieved through elevation of the affected area (portion of the supported arm 1b). Conventional slings only allow the supported arm 1b to be supported at roughly a 90 degree angle at the elbow. This new design allows the patient to elevate the affected hand and forearm, decreasing the angle between the humerus if and the radius/ulna to an angle at the elbow that is less than 90 degrees. This conversion, or change of angle at the elbow is facilitated while maintaining full support and comfort of the supported arm 1b of the user 1.

Figure 12:
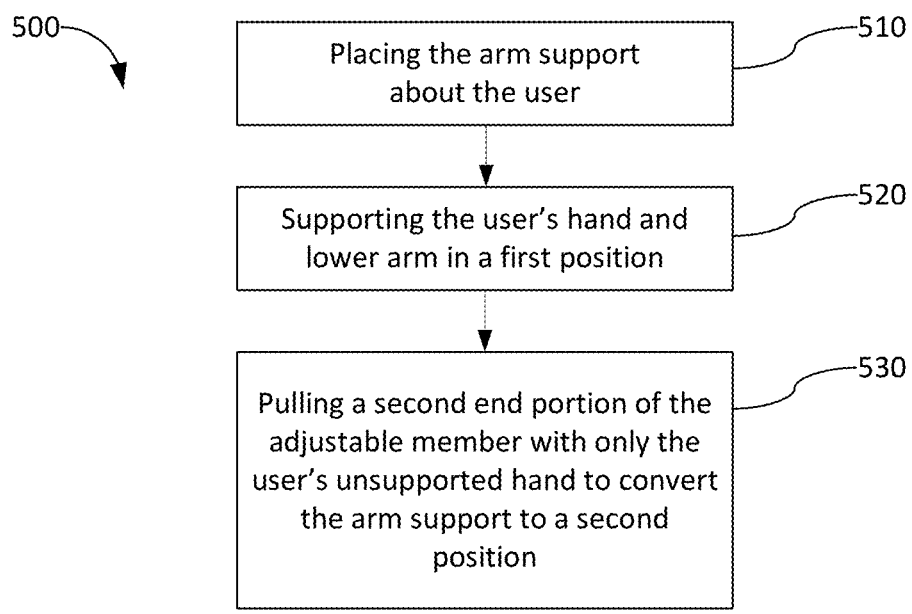
FIG. 12 is a method of converting the arm support of FIGS. 1-10 from a first position to a second position.

FIG. 12 shows an illustrative method 500 of converting the illustrative arm support 100 of FIGS. 1-9 from a first position to a second position. The arm support 100 configured to support a force corresponding to at least a portion of the weight of a supported arm 1b of a user 1 onto an opposite shoulder of the user 1. The illustrative method 500 may include the following steps:

1) providing the arm support 100 to a user 1

2) placing the arm support about the user such that the first end portion of the force distribution portion is proximate the shoulder of the user (step 510)

3) supporting the user's hand and lower arm in a first position along a first axis substantially perpendicular to the longitudinal axis 1c of the body and proximate the waist of the user 1 (Step 520)

4) converting the arm support to support the user's hand and lower arm in a second position, wherein the second position the lower arm and hand of the user are oriented along a second axis extending from the lower rib on the supported side of the user's body to the shoulder joint on the unsupported side of the user's body with the hand of the user located distal and elevated above the waist of the user, the user's hand supported such that the hand is proximate the pectoral muscle on the unsupported side of the user's body than the arm of the user being supported by the arm support (Step 530).

The illustrative method further including the converting step being accomplished solely by moving the second end of the adjustment member away from the locking element in a substantially downward direction along the longitudinal axis of the user using only the user's free hand.

In some embodiments, the method includes converting the arm support from the first position to the second position by moving the second end of the adjustment member away from the locking element. In other embodiments, when the arrangement of parts is reversed (as described with respect to the arm support apparatus described above) the second end of the adjustment member may be adjusted downward toward the waist of the user. This direction of movement depends on which of the locking element 72 and the adjustment member 74 is attached to the force distribution portion 20, and which is attached to the support portion 30.

Various examples have been described. These and other examples, and any combination of examples are within the scope of the following claims. Although this disclosure has been provided with reference to illustrative embodiments, it is not meant to be construed in a limiting sense. One of skill in the art will recognize that other various applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. An arm support for transferring and supporting a force corresponding to at least a portion of the weight of a supported arm of a user onto an opposite unsupported shoulder of the user when worn, the arm support comprising:

a force distribution portion extending from a first end portion to a second end portion, the force distribution portion including a front shoulder cap and a rear shoulder cap, the front shoulder cap having a curved construction including a three-dimensional shape that conforms to the shoulder of the unsupported arm of the user prior to being donned on the unsupported shoulder of the user, wherein the force distribution portion is configured to distribute the force to the shoulder girdle on the unsupported side of the user's body; and a support portion adapted to support the user's lower arm, the support portion extending from a first end portion to a second end portion opposite the first end portion, wherein the support portion first end portion is adjacent the force distribution portion second end portion, and wherein the support portion second end portion is configured to be adjustably couplable to the force distribution portion first end portion, wherein the support portion comprises:

a first layer extending from the support portion first end portion to an overlap region; and a hand portion first layer extending from the overlap region to the second end portion of the support portion, wherein at least a portion of the first layer and at least a portion of the hand portion first layer overlap in the overlap region, wherein the first layer and the hand portion first layer define a first longitudinal side end portion and an opposite second longitudinal side end portion of the support portion, wherein the first longitudinal side end portion extends from the support portion first end portion to the support portion second end portion, and the second longitudinal side end portion extends from the support portion first end portion to the support portion second end portion, wherein a distance between the first longitudinal side end portion and the second longitudinal side end portion defines a width of the support portion, and wherein when worn, the support portion is configured to support a user's arm cradled in a hammock arrangement at a location in between the first longitudinal side end portion and the second longitudinal side end portion, wherein the first and second longitudinal side end portions are arranged such that a central portion of the first layer in between the first longitudinal side end portion and the second longitudinal side end portion is configured to cradle the arm from below with the first and second longitudinal side end portions extending upward away from the central portion, and wherein when worn, the user's arm is receivable and egressable through an arm egress opening defined between the first longitudinal side end portion and the second longitudinal side end portion, wherein the first layer and the hand portion first layer are coupled together at a first joining region located along the first longitudinal side end portion in the overlap region, and at a second joining region located along the second longitudinal side end portion in the overlap region.

2. The arm support of claim 1, wherein the hand portion further comprising a hand portion second layer that crosses and extends beyond the overlap region in both directions along the support axis and is joined to the first layer and the hand portion first layer in the joining regions, wherein the hand portion is configured to support the hand in a first hand position or a second hand position, wherein in the first hand position the first layer and the hand portion first layer are configured to support the back of a user's hand, and wherein in the second hand position, the hand portion second layer is configured to support the back of the user's hand, and further wherein in the second position, the hand portion second layer is disposed between the hand portion first layer and the back side of the user's hand.

3. The arm support of claim 1, wherein the front shoulder cap has a generally semi-circular shaped portion.

4. The arm support of claim 1, wherein a mid-point of the shoulder cap is configured to be positioned over the anterior head of the humerus and the pectoralis muscles of the user on the unsupported side of the body of the user when supporting the opposite arm of the user.

5. The arm support of claim 1, wherein the force distribution portion further comprises a locking element proximate the force distribution portion and positioned such that the locking element provides a downward force on the force distribution portion to keep the force distribution in place to provide an even distribution of force through the shoulder girdle.

6. The arm support of claim 1, further comprising an adjustment device including:
a locking element; and
an elongate adjustment member having a first end portion and a second end portion opposite the first end portion, the adjustment member slidably couplable to the locking element between the first and second end portions of the adjustment member;

wherein the second end portion of the support portion is fixedly coupled to the first end portion of the adjustment member, and wherein the locking element is fixedly coupled to the force distribution portion.

7. The arm support of claim 6, wherein the support portion has a length extending from the first end portion to the second end portion of the support portion along a support axis, and wherein the adjustment member has a length extending from the first end portion to the second end portion of the adjustment member along an adjustment member axis, wherein the support axis and the adjustment member axis are arranged within +/−45 degrees of one another at a coupling point between the support portion and the adjustment member, the coupling point located at the second end portion of the support portion.

8. The arm support of claim 1, wherein the force distribution portion is adapted to fit distally over the deltoid muscle and the shaft of the humerus and medially over the clavicle extending across the upper trapezius muscle and the scapula of the unsupported side of the user when supporting the supported arm, and wherein the three-dimensional shape is configured to distribute the force evenly.

9. An arm support comprising:
a support portion adapted to support a user's arm, wherein the support portion extends from a first end portion to a second end portion, the support portion having:
a first longitudinal side end portion extending from the support portion first end portion to the support portion second end portion; and
a second longitudinal side end portion opposite the first longitudinal side end portion extending from the support portion first end portion to the support portion second end portion,
wherein the support portion comprises a width extending from the first longitudinal side end portion to the second longitudinal side end portion; and
a force distribution portion coupled to the support portion, wherein the force distribution portion is configured to distribute a force corresponding to a user's supported arm onto an opposite shoulder of a user,
the support portion further comprising:
a first layer extending from the first end portion to an overlap region; and
a hand portion having a hand portion first layer and a hand portion second layer the hand portion first layer extending from the overlap region to the second end portion of the support portion, wherein at least a portion of the hand portion first layer overlaps with and is coupled to at least a portion of the first layer in the overlap region to form an egress opening between the hand portion first layer and the first layer,
wherein the hand portion is configured to support the hand in a first position or a second position, wherein in the first position the back side of a user's hand is supported by the hand portion first layer and the first layer,
wherein in the second position, the back side of a user's hand is supported by the hand portion second layer with the hand portion second layer disposed between the hand portion first layer and the back side of a user's hand,
wherein the support portion and the hand portion and are joined together at joining regions near the first and second longitudinal side end portions, and
wherein the first and second longitudinal side end portions are arranged such that a central portion of the first layer in between the first longitudinal side end portion and the second longitudinal side end portion is configured to cradle the arm from below with the first and second longitudinal side end portions extending upward away from the central portion.

10. The arm support of claim 9, wherein the curved three-dimensional form is constructed by cutouts and seams in the force distribution portion.

11. The arm support of claim 9, wherein the force distribution portion comprises a fabric material joined at seams, wherein the seams are positioned to create the curved three-dimensional form.

12. The arm support of claim 9, wherein the force distribution portion includes a front shoulder cap that includes a curved three-dimensional form that conforms to a shoulder of a user prior to be donned on an unsupported shoulder of a user.

13. An arm support for transferring and supporting a force corresponding to at least a portion of the weight of a supported arm of a user onto an opposite unsupported shoulder of the user when worn, the arm support comprising:
 a force distribution portion adapted to conform to the shoulder of the unsupported arm, the force distribution portion configured to distribute the force evenly to the shoulder girdle on the unsupported side of the user's body, the force distribution portion extending from a first end portion to a second end portion opposite the first end portion; and
 a support portion adapted to support the user's lower arm and hand, the support portion extending from a first end portion adjacent to the force distribution portion to a second end portion that is configured to be adjustably couplable to the force distribution portion first end portion, the support portion comprising:
 a first layer; and
 a hand portion first layer,
 wherein the first layer extends from the support portion first end portion to an overlap region, and the hand portion first layer extends from the overlap region to the second end portion of the support portion, wherein at least a portion of the first layer and at least a portion of the hand portion first layer overlap in the overlap region, wherein the first layer and the hand portion first layer define a first longitudinal side end portion and an opposite second longitudinal side end portion of the support portion,
 wherein the first longitudinal side end portion extends from the support portion first end portion to the support portion second end portion, and the second longitudinal side end portion extends from the support portion first end portion to the support portion second end portion,
 wherein a distance between the first longitudinal side end portion and the second longitudinal side end portion define a width of the support portion, wherein the first and second longitudinal side end portions are arranged such that a central portion of the first layer in between the first longitudinal side end portion and the second longitudinal side end portion is configured to cradle the arm from below with the first and second longitudinal side end portions extending upward away from the central portion, and wherein when worn, the user's arm is receivable and egressable through an arm egress opening defined between the first longitudinal side end portion and the second longitudinal side end portion,
 wherein the first layer and the hand portion first layer are coupled together at a first joining region located along the first longitudinal side end portion in the overlap region, and at a second joining region located along the second longitudinal side end portion in the overlap region such that a hand egress opening extends a majority of the width between the first longitudinal side end portion and the second longitudinal side end portion.

14. The arm support of claim 13, wherein the force distribution portion coupled to the support portion, wherein the force distribution portion is configured to distribute a force corresponding to a user's supported arm onto an opposite shoulder of a user, wherein the force distribution portion includes a front shoulder cap that includes a curved three-dimensional form that conforms to a shoulder of a user prior to be donned on an unsupported shoulder of a user.

15. The arm support of claim 13, wherein the first layer and the hand portion first layer are not joined to each other across a majority of the width at the overlap region such that a user's hand can be egressed at locations located across the majority of the overlap region in between the first joining region and the second joining region.

16. The arm support of claim 13, wherein the user's hand can be egressed through the overlap region at a location where a central axis of the support portion intersects the overlap region, wherein the central longitudinal axis is located at a mid-point between the first longitudinal side end portion and the second longitudinal side end portion.

17. The arm support of claim 13, wherein the support portion is configured, when worn, to support a user's arm cradled in a hammock arrangement at a location in between the first longitudinal side end portion and the second longitudinal side end portion, wherein the support portion is configured to support the users arm along a central axis of the support portion, and wherein the central axis is disposed centrally between the first longitudinal side end portion and the second longitudinal side end portion.

18. The arm support of claim 13, wherein when the support portion is worn such that the support portion is folded along a central longitudinal axis, the central longitudinal axis being disposed between the first longitudinal side end portion and the second longitudinal side end portion, an arm egress opening remains open between the first longitudinal side end portion and the second longitudinal side end portion to receive and cradle the arm in the hammock arrangement along the central longitudinal axis.

19. The arm support of claim 13, wherein the hand portion further comprising a hand portion second layer that crosses and extends beyond the overlap region in both directions along the support axis and is joined to the first layer and the hand portion first layer in the joining regions,
 wherein the hand portion is configured to support the hand in a first hand position or a second hand position, wherein in the first hand position the first layer and the hand portion first layer are configured to support the back of a user's hand, and wherein in the second hand position, the hand portion second layer is configured to support the back of the user's hand, and further wherein in the second position, the hand portion second layer is disposed between the hand portion first layer and the back side of the user's hand.

* * * * *